US012714659B2

(12) United States Patent
Kumagai et al.

(10) Patent No.: US 12,714,659 B2
(45) Date of Patent: Aug. 25, 2026

(54) COSMETIC

(71) Applicant: SHISEIDO COMPANY, LTD., Tokyo (JP)

(72) Inventors: Mayu Kumagai, Tokyo (JP); Motoharu Kimura, Tokyo (JP); Tetsuya Kanemaru, Tokyo (JP); Yuka Iwahashi, Tokyo (JP)

(73) Assignee: SHISEIDO COMPANY, LTD., Tokyo (JP)

( * ) Notice: Subject to any disclaimer, the term of this patent is extended or adjusted under 35 U.S.C. 154(b) by 652 days.

(21) Appl. No.: 18/043,558

(22) PCT Filed: Sep. 24, 2021

(86) PCT No.: PCT/JP2021/035151

§ 371 (c)(1),
(2) Date: Feb. 28, 2023

(87) PCT Pub. No.: WO2022/071143

PCT Pub. Date: Apr. 7, 2022

(65) Prior Publication Data

US 2023/0263714 A1 Aug. 24, 2023

(30) Foreign Application Priority Data

Sep. 30, 2020 (JP) ................................. 2020-164366

(51) Int. Cl.

| | |
|---|---|
| ***A61K 8/36*** | (2006.01) |
| ***A61K 8/02*** | (2006.01) |
| ***A61K 8/29*** | (2006.01) |
| ***A61Q 1/12*** | (2006.01) |

(52) U.S. Cl.
CPC .............. *A61K 8/361* (2013.01); *A61K 8/022* (2013.01); *A61K 8/29* (2013.01); *A61Q 1/12* (2013.01); *A61K 2800/412* (2013.01)

(58) Field of Classification Search
CPC ...................................................... A61K 8/361
See application file for complete search history.

(56) References Cited

FOREIGN PATENT DOCUMENTS

| | | | |
|---|---|---|---|
| JP | H06-305935 | A | 11/1994 |
| JP | H11-035440 | A | 2/1999 |
| JP | 2000-169342 | A | 6/2000 |
| JP | 2002-047138 | A | 2/2002 |
| JP | 2007-186463 | A | 7/2007 |
| JP | 2012-020982 | A | 2/2012 |
| JP | 2012-149005 | A | 8/2012 |
| JP | 2018-168145 | A | 11/2018 |

OTHER PUBLICATIONS

Office Action issued in corresponding Chinese Patent Application No. 202180053440.1 dated Oct. 28, 2024.
Cosmetics crafts, Chapter tannin, p. 209, China Light Industry Press, Sep. 2007.
Modern Custom Chemicals Wandollar, pp. 570-571, Beijing Metallurgical Industry Press, Mar. 2000.
Office Action issued in corresponding Chinese Patent Application No. 202180053440.1 dated Apr. 10, 2025.
Sawada, Kohei, “Development of a New Metal Soap—The size of the particles is reduced to one tenth of the conventional size—,” Japan Energy and Technology Intelligence, vol. 50, No. 8, Jul. 2002, pp. 121-122.
International Searching Authority, “International Search Report,” issued in connection with International Patent Application No. PCT/JP2021/035151, dated Nov. 22, 2021.
International Searching Authority, “Written Opinion,” issued in connection with International Patent Application No. PCT/JP2021/035151, dated Nov. 22, 2021.

*Primary Examiner* — Paul V Ward
(74) *Attorney, Agent, or Firm* — Foley & Lardner LLP

(57) ABSTRACT

The invention relates to a cosmetic containing fatty acid magnesium salt particles and fine particle titanium oxide in which the fatty acid magnesium salt particles have a fatty acid having 12 to 22 carbon atoms, an aspect ratio expressed by the following formula (1) of 1.0 or more and 2.0 or less and an average thickness of 250 to 600 nm.

Aspect Ratio=Major axis diameter of Particle (μm)/Minor axis diameter of Particle (μm)    formula (1).

6 Claims, No Drawings

COSMETIC

CROSS-REFERENCE TO RELATED APPLICATIONS

The present application claims priority under 35 U.S.C. § 371 to International Patent Application No. PCT/JP2021/035151, filed Sep. 24, 2021, which claims priority to and the benefit of Japanese Patent Application No. 2020-164366, filed on Sep. 30, 2020. The contents of these applications are hereby incorporated by reference in their entireties.

TECHNICAL FIELD

The present invention relates to a cosmetic containing fatty acid magnesium.

BACKGROUND ART

Of cosmetics, powdered cosmetics often have images of powdery sensation, dryness, squeakiness and the like and thus are required to have moistness, and of powdered cosmetics, cosmetics which are used for finishing, such as loose powders, are required to have use feeling such as transparency and gloss rather than covering property.

Patent Literature 1 describes a powdered cosmetic containing a metallic soap, and Patent Literature 2 discloses that a solid powder cosmetic having excellent formability, impact resistance, durability and the like is obtained when a specific amount of metallic soap microparticles having a specific particle size are used.

CITATION LIST

Patent Literature

Patent Literature 1: JP-A-H6-305935
Patent Literature 2: JP-A-2000-169342

SUMMARY OF INVENTION

Technical Problem

As described in Patent Literature 1, metallic soaps are blended generally for improving the impact resistance and are usually blended for improving the impact resistance rather than improving the use feeling. Accordingly, when the amount thereof increases, removal becomes difficult, and influence on the use feeling, such as squeakiness, may be caused.

Moreover, the powder cosmetic described in Patent Literature 2 has room for improvement in terms of the use feeling.

A purpose of the invention is to provide a cosmetic having excellent use feeling such as moistness, transparency and gloss.

Solution to Problem

As a result of intensive investigation to solve the problem, the present inventors have found that a cosmetic having excellent use feeling can be obtained when fatty acid magnesium salt particles having an aspect ratio within a specific range and fine particle titanium oxide are contained.

That is, the invention relates to the cosmetic below.

[1] A cosmetic containing fatty acid magnesium salt particles and fine particle titanium oxide, wherein the fatty acid of the fatty acid magnesium salt particles has 12 to 22 carbon atoms, the aspect ratio of the fatty acid magnesium salt particles expressed by the following formula (1) is 1.0 or more and 2.0 or less, and the average thickness of the fatty acid magnesium salt particles is 250 to 600 nm:

$$\text{the aspect ratio} = \text{the major axis diameter of a particle } (\mu m)/\text{the minor axis diameter of the particle } (\mu m) \quad \text{formula (1)}.$$

[2] The cosmetic described in [1] which further contains an oil-based component.

[3] The cosmetic described in [1] or [2], wherein the fine particle titanium oxide content is 10 mass % or less.

[4] The cosmetic described in [2] or [3] which contains a liquid oil-based component as the oil-based component.

[5] The cosmetic described in any one of [2] to [4], wherein the oil-based component content is 10 mass % or less.

[6] The cosmetic described in any one of [1] to [5], wherein the cosmetic is a powder cosmetic.

Advantageous Effects of Invention

According to the invention, a cosmetic having excellent use feeling such as moistness, transparency and gloss can be provided.

DESCRIPTION OF EMBODIMENTS

The cosmetic of the invention contains specific fatty acid magnesium salt particles as a metallic soap.

The fatty acid magnesium salt particles of the invention are composed of a magnesium salt of a divalent fatty acid having 12 to 22 carbon atoms. The particles can be prepared by a metathesis method in which a fatty acid-alkaline compound salt obtained by reacting a monovalent alkaline compound with a fatty acid having 12 to 22 carbon atoms and a divalent magnesium salt are reacted in an aqueous solution.

The fatty acid used as the raw material of the fatty acid-alkaline compound salt is not particularly restricted as long as the fatty acid has 12 to 22 carbon atoms. That is, the fatty acid may be a naturally derived fatty acid or a synthetic fatty acid, may be a saturated fatty acid or an unsaturated fatty acid and may be a linear or branched fatty acid. The fatty acid may contain a functional group such as a hydroxyl group, an aldehyde group and an epoxy group in its structure. The fatty acid is preferably a linear saturated fatty acid.

The fatty acid has 12 or more carbon atoms and thus can give excellent use feeling to the cosmetic. Because the number of the carbon atoms is 22 or less, the fatty acid is industrially easily obtained, and the solubility of the obtained fatty acid-alkaline compound salt in water does not decrease significantly. Thus, the productivity is high. The number of the carbon atoms of the fatty acid is preferably 12 to 18, more preferably 14 (which means that the fatty acid magnesium is magnesium myristate).

Examples of the fatty acid include lauric acid, myristic acid, myristoleic acid, palmitic acid, palmitoleic acid, stearic acid, oleic acid, linoleic acid, arachic acid, behenic acid, erucic acid, hydroxystearic acid, epoxystearic acid and the like. Of these, myristic acid is preferable. When a mixed fatty acid is used, the myristic acid content of the fatty acid is preferably 50% or more, more preferably 60% or more, further preferably 70% or more.

The aspect ratio of the fatty acid magnesium salt particles of the invention is 1.0 or more and 2.0 or less, preferably 1.0 or more and 1.6 or less, more preferably 1.0 or more and 1.5 or less.

In the invention, the aspect ratio of a particle corresponds to the following formula (1), namely the value obtained by dividing the major axis diameter of a fatty acid magnesium salt particle by the minor axis diameter (=major axis diameter/minor axis diameter).

Aspect Ratio=Major axis diameter of Particle (μm)/ Minor axis diameter of Particle (μm) formula (1)

An aspect ratio which is closer to 1.0 means that the shape of the particle is closer to a square or a circle. The fatty acid magnesium salt particles of the invention preferably have a shape which is close to a square.

As a result, spreading on the skin improves, and the use feeling is excellent.

Here, the "major axis diameter" of a particle is the length of the major axis of the particle and more specifically corresponds to the width of the particle where the distance between two parallel lines sandwiching the particle becomes the maximum. The "minor axis diameter" of the particle is the length of the minor axis of the particle and more specifically corresponds to the width of the particle measured on the straight line which passes through the midpoint of the major axis and which intersects the major axis at right angles. Here, the average thickness of particles is the average determined by measuring the lengths of side faces of 10 particles while setting the faces of the fatty acid magnesium salt particles with the largest areas as front faces. The average thickness of the particles is a value measured based on two-dimensional projection images of the particles (specifically, SEM images).

The average thickness of the fatty acid magnesium salt particles of the invention is 250 to 600 nm. Due to the thickness, the particles easily dissolve even under mild mixing conditions (production method) for the cosmetic. Moreover, the cosmetic is easily applied to the skin evenly, and the texture after the application can also be improved. When the average thickness is 250 nm or more, the handling property of the fatty acid magnesium salt particles is excellent during the addition to the cosmetic, and there is no risk of reduction in the workability. The average thickness of the particles is more preferably 280 to 450 nm, particularly preferably 300 to 450 nm. When the average thickness of 300 to 450 nm is satisfied, the effects of action of the invention are obtained further more stably.

The cosmetic of the invention has excellent use feeling such as moistness, transparency and gloss because fatty acid magnesium salt particles having the specific properties and fine particle titanium oxide are used in combination. Moreover, finishing with natural gloss which is different from the gloss of an oil component or pearlescent powder can be achieved. This is speculated to be because spreading on the skin improves because the fatty acid magnesium salt particles in the invention have the specific aspect ratio.

The particle index of the fatty acid magnesium salt particles of the invention is preferably 1.5 or more and 8.0 or less. Due to the particle index, the cosmetic is easily applied to the skin evenly, and the texture after the application can be maintained for a long time. When the particle index is 1.5 or more, the dispersibility of the fatty acid magnesium salt particles is excellent during the addition to the cosmetic, and there is no risk of reduction in the workability. The particle index of the particles is preferably 1.5 or more and 6.0 or less, more preferably 2.0 or more and 5.0 or less. When the particle index of 2.0 or more and 5.0 or less is satisfied, the effects of action of the invention are obtained further more stably.

Here, in the invention, the particle index of the particles corresponds to the following formula (2), namely the value obtained by dividing the value obtained by dividing the major axis diameter of the fatty acid magnesium salt particles by the minor axis diameter (=major axis diameter/minor axis diameter) by the average thickness of the particles [=(major axis diameter/minor axis diameter)/average thickness of particles].

Particle Index=[(Major axis diameter of Particles (μm)/Minor axis diameter of Particles (μm))/ Average Thickness of Particles (nm)]×1000 formula (2)

The fatty acid magnesium salt particles of the invention have a narrow particle size distribution and thus can uniformly exist in the cosmetic, and the effects of action of the invention (especially the improvement of the texture of the cosmetic) are exhibited more stably. Specifically, the median size of the fatty acid magnesium salt particles is preferably 10.0 to 40.0 μm, and the particle size digest A expressed by the following formula (3) is preferably 2.5 or less.

Particle Size Digest $A=(D90-D10)/D50$ formula (3)

(Here, 10.0≤D50≤40.0.)

D10: the 10% cumulative size (μm) of the fatty acid magnesium salt particles on a volumetric basis D50: the median size (μm) of the fatty acid magnesium salt particles on a volumetric basis D90: the 90% cumulative size (μm) of the fatty acid magnesium salt particles on a volumetric basis In the invention, the particle size digest A is calculated from the particle sizes measured by the Microtrac laser diffraction method. When the particle size digest A is 2.5 or less, the fatty acid magnesium salt particles in the cosmetic have a uniform particle size, and the dispersibility of the cosmetic is excellent. Moreover, the productivity does not decrease, and a cosmetic having an aimed texture can be produced. The particle size digest A more preferably satisfies the relation 0.5≤A≤2.5. When the relation 0.5≤A≤2.5 is satisfied, the effects of action of the invention are obtained further more stably. When the particle size digest A is 0.5 or more, the yield does not decrease, and industrially stable production is possible.

Here, when a cumulative curve is drawn in which the total volume of the powder population is regarded as 100% in the formula (3), the particle sizes at 10%, 50% and 90% of the cumulative curve are referred to as the 10% cumulative size (D10), the 50% median size (D50; median size) and the 90% cumulative size (D90) (μm), respectively. Here, the particle size means the particle size of a primary particle. When the particles cohere during the measurement, the particles are measured in a state of being dispersed with ultrasonic wave or the like.

The particle size digest A can be adjusted by appropriately adjusting the concentration of the fatty acid-alkaline compound salt, the temperature of the reaction of the fatty acid-alkaline compound salt and the magnesium salt and the dropping speed for dropping the magnesium salt-containing aqueous solution to the fatty acid-alkaline compound salt-containing aqueous solution. Moreover, when the particles have a broad particle size distribution, namely, a large particle size digest A value, the particle size digest A can be adjusted through sorting using a sieve such as 100 mesh, 200 mesh and 330 mesh in the posttreatment.

The Microtrac laser diffraction method used here is a method for determining the particle size distribution using scattered light obtained by irradiating particles with laser beam. In the invention, the measurement is made by the wet method in which the sample is fed while an organic solvent into which the fatty acid magnesium salt particles do not dissolve, such as organic solvents including ethanol, isopropyl alcohol and the like, circulates. Moreover, the measurement target in the invention has a particle size in the range of 0.1 μm to 200 μm, and the value expressed by the formula (3) is the particle size digest A. In the invention, the measurement can be made, for example, using Microtrac MT-3000 manufactured by Nikkiso Co., Ltd.

The median size (D50) of the fatty acid magnesium salt particles of the invention on a volumetric basis is preferably 10.0 to 40.0 μm. Due to the particle size, the texture upon use is excellent. The median size of the fatty acid magnesium salt particles is preferably 13.0 to 35.0 μm, more preferably 15.0 to 25.0 μm. The particle size can be measured by the Microtrac laser diffraction method like the particle size digest A described above.

The shape of the fatty acid magnesium salt particles of the invention is not particularly limited but is preferably plate-like in view of the use feeling.

The fatty acid magnesium salt particles which satisfy the specific properties can be prepared by a metathesis method in which a fatty acid-alkaline compound salt obtained by reacting a monovalent alkaline compound with a fatty acid having 12 to 22 carbon atoms and a divalent magnesium salt are reacted in an aqueous solution. When the magnesium salt-containing aqueous solution and the fatty acid-alkaline compound salt-containing aqueous solution, which are prepared separately by metathesis reaction, are mixed, the magnesium salt-containing aqueous solution is preferably dropped gradually into the fatty acid-alkaline compound salt-containing aqueous solution, as described below.

The monovalent alkaline compound used as the raw material of the fatty acid-alkaline compound salt is a hydroxide of an alkali metal (sodium, potassium or the like), ammonia, an amine such as monoethanolamine, diethanolamine and triethanolamine or the like. Because the solubility of the resulting fatty acid-alkaline compound salt in water is high, a hydroxide of an alkali metal such as sodium and potassium is preferable.

The fatty acid-alkaline compound salt used in the invention is obtained by reacting the monovalent alkaline compound and the fatty acid generally at a temperature which is the melting point of the fatty acid or higher and at which the fatty acid does not decompose, preferably at 100° C. or lower, more preferably at 50 to 100° C., further preferably at 60 to 95° C., particularly preferably at 80 to 95° C.

The fatty acid magnesium salt particles of the invention can be obtained, for example, by reacting the fatty acid-alkaline compound salt obtained above and a magnesium salt in an aqueous solution. The magnesium salt is specifically a salt of inorganic magnesium and an inorganic acid or an organic acid. Examples of the magnesium salt include magnesium chloride, magnesium sulfate, magnesium acetate and the like. In particular, chloride of magnesium and sulfated magnesium are preferable because of the high solubility in water and the efficient reaction with the fatty acid-alkaline compound salt.

The reaction of the fatty acid-alkaline compound salt and the divalent magnesium salt is conducted specifically by preparing a magnesium salt-containing aqueous solution and a fatty acid-alkaline compound salt-containing aqueous solution separately and then mixing the solutions. For example, the reaction is conducted by adding the magnesium salt-containing aqueous solution to the fatty acid-alkaline compound salt-containing aqueous solution or adding the both into a separate reaction bath.

Regarding mixing of the fatty acid-alkaline compound salt-containing aqueous solution and the magnesium salt-containing aqueous solution, when the magnesium salt-containing aqueous solution is fed into the fatty acid-alkaline compound salt-containing aqueous solution at once, for example, the shapes of the obtained fatty acid magnesium salt particles may become ununiform, and the aspect ratio of the particles may become large. Thus, in the invention, the magnesium salt-containing aqueous solution is preferably dropped gradually at an appropriate speed to the fatty acid-alkaline compound salt-containing aqueous solution.

The dropping speed is preferably 0.005 to 0.8 mol/minute per unit time, further preferably 0.01 to 0.5 mol/minute. By mixing at the dropping speed, the exchange reaction of the alkali and the magnesium can be advanced gently, and fatty acid magnesium salt particles having a moderate aspect ratio and a moderate thickness can be obtained. When the speed is 0.005 mol/minute or more, fatty acid magnesium salt particles having a desired aspect ratio and a desired thickness can be obtained. On the other hand, when the dropping speed per unit time is 0.8 mol/minute or less, the fatty acid magnesium salt particles have a uniform shape, and the particles have a desired aspect ratio and a desired thickness. Thus, the particle size is not uneven, which is excellent.

The unit of the magnesium salt dropped, "mol/minute", is the number of moles of the magnesium salt dropped per 1 mole of the fatty acid-alkaline compound per unit time.

The concentration of the fatty acid-alkaline compound salt during the production of the fatty acid magnesium salt is generally 1 mass % to 20 mass %, preferably 5 mass % to 15 mass % in view of the productivity of the fatty acid magnesium salt and in view of the handling property of the fatty acid-alkaline compound salt-containing aqueous solution or the obtained fatty acid magnesium salt slurry. The concentration of the fatty acid-alkaline compound salt is preferably 1 mass % or more because the productivity of the fatty acid magnesium salt is excellent. When the concentration is 20 mass % or less, the viscosity of the fatty acid-alkaline compound salt-containing aqueous solution or the obtained fatty acid magnesium salt slurry does not increase, and uniform reaction is possible. Here, the concentration of the magnesium salt in the magnesium salt-containing aqueous solution is generally 10 mass % to 50 mass %, preferably 10 mass % to 40 mass % in view of the productivity of the fatty acid magnesium salt and in view of the handling property of the fatty acid-alkaline compound salt-containing aqueous solution or the obtained fatty acid magnesium salt slurry.

The reaction of the fatty acid-alkaline compound salt and the magnesium salt is conducted under the temperature conditions which one skilled in the art generally uses considering the solubility of the fatty acid-alkaline compound salt. The temperature is preferably 50 to 100° C., more preferably 60 to 95° C. When the reaction temperature is 50° C. or higher, the reaction rate of the fatty acid-alkaline compound salt and the magnesium salt is excellent.

For the purpose of stabilizing the fatty acid magnesium salt slurry and improving the productivity of the fatty acid magnesium salt during the reaction of the fatty acid-alkaline compound salt and the magnesium salt, a polyalkylene glycol ether, especially a triblock ether having a structure in which an oxypropylene block is between oxyethylene blocks (EO-PO-EO), is preferably contained in the fatty acid magnesium salt slurry. The polyalkylene glycol ether content of the fatty acid magnesium salt slurry is generally 0.01 parts by mass to 5 parts by mass, preferably 0.05 parts by mass to 2 parts by mass based on 100 parts by mass of the fatty acid-alkaline compound salt. The polyalkylene glycol ether may be contained in the reaction system before the reaction of the monovalent alkaline compound and the fatty acid and may also be contained in the reaction system before the reaction of the fatty acid-alkaline compound salt and the magnesium salt.

A fatty acid magnesium salt cake with a water content that is reduced through separation with one dehydrator, a filter press or the like is obtained by the method. The fatty acid magnesium salt cake with a reduced water content is dried with a rotary dryer, a flash dryer, a ventilated tray dryer, a vacuum tray dryer, a spray dryer, a fluidized bed dryer or the like.

In the invention, it is necessary that the fatty acid magnesium salt cake is dried at $(\alpha-60)°$ C.$\leq\alpha\leq(\alpha-30)°$ C. regarding the contained water evaporation peak top temperature ($\alpha°$ C.) of the produced fatty acid magnesium salt. Here, the contained water evaporation peak top temperature is the top peak of the peak in the temperature range in which the residual water contained in the fatty acid magnesium salt which cannot be removed by the drying starts to desorb. For example, the contained water evaporation peak top temperature is 102.1° C. in a heat absorption graph of magnesium myristate by differential thermal analysis (DSC). The specific drying temperature differs with the kind of the obtained fatty acid magnesium salt but is 72° C. or lower in the case of magnesium myristate, for example. When the drying treatment is conducted at a temperature higher than 72° C., the microparticles adhere to each other, and the particle thickness is apt to be large. On the other hand, when the drying treatment is conducted at a temperature lower than 40° C., the drying property decreases, and a large amount of water remains in the compound. The productivity may thus decrease.

In the above manner, the fatty acid magnesium salt particles can be produced.

The fatty acid magnesium salt particle content of the cosmetic of the invention is preferably 1 to 60 mass %, more preferably 5 to 40 mass %, particularly preferably 10 to 20 mass % in view of giving use feeling.

The cosmetic of the invention contains fine particle titanium oxide. Because the specific fatty acid magnesium salt particles and fine particle titanium oxide are used in combination, use feeling such as moistness, transparency and gloss improves.

The average primary particle size of the fine particle titanium oxide is preferably 0.001 to 0.1 μm, more preferably 0.01 to 0.05 μm because moistness can be given and because finishing with transparency can be given after the application. Use of titanium oxide particles having an average particle size of 0.2 μm or more, namely so-called pigment grade particles, results in white unnatural finishing while the covering property is high. In the invention, however, because the fine particle titanium oxide is used, natural finishing with transparency can be achieved, and moistness can be given.

The fine particle titanium oxide content of the cosmetic is preferably 10 mass % or less, more preferably 1 to 10 mass %, particularly preferably 1 to 7 mass % because moistness can be given.

The cosmetic of the invention preferably further contains an oil-based component. This results not only in improvement of moistness but also in inhibition of fluttering and dusting of the powder, which are major problems of powdered cosmetic products.

The oil-based component is a liquid oil-based component or a solid oil-based component, and a liquid oil-based component is preferably contained because powder cohesion can be reduced and also in view of the product stability.

Examples of the liquid oil-based component include silicone oil, avocado oil, camellia oil, macadamia nut oil, corn oil, olive oil, rapeseed oil, egg yolk oil, sesame oil, persic oil, wheat germ oil, sasanqua camellia oil, castor oil, linseed oil, safflower oil, cottonseed oil, perilla oil, soybean oil, peanut oil, tea seed oil, kaya oil, rice bran oil, Chinese tung oil, Japanese tung oil, jojoba oil, germ oil, triglycerin, glyceryl trioctanoate, glyceryl triisopalmitate and the like. Two or more kinds thereof may be used in combination.

Examples of the solid oil-based component include hydrocarbons/waxes such as solid paraffin, ceresin, microcrystalline wax, polyethylene wax, hydrogenated oil, beeswax, Japan wax, spermaceti wax and candelilla wax, higher fatty acids such as stearic acid, lauric acid, myristic acid and behenic acid, higher alcohols such as cetyl alcohol, stearyl alcohol and lauryl alcohol and the like. Two or more kinds thereof may be used in combination.

The oil-based component content of the cosmetic is preferably 10 mass % or less, more preferably 1 to 10 mass %, particularly preferably 2 to 5 mass % in view of the product stability and the use feeling.

The cosmetic of the invention may further contain inorganic powder or organic powder.

The inorganic powder is an inorganic pigment such as zinc oxide, red iron oxide, yellow iron oxide and black iron oxide, mica, talc or the like.

In the invention of the present application, mica is blended preferably in an amount of 5 to 80 mass %, more preferably 20 to 60 mass %, in view of improvement of gloss, improvement of spreading on the skin and improvement of transparency. The mica is natural mica, synthetic fluorphlogopite, synthetic fluorphlogopite iron, sericite or the like, and synthetic fluorphlogopite is more preferable.

The organic powder may be an organic pigment such as a natural colorant.

The powder may be subjected to surface treatment with a fluorine compound, a silicone compound, a fatty acid or the like.

The cosmetic of the invention can appropriately contain another component which is generally used for cosmetic products and the like in addition to the components in the range which does not impair the effects of the invention. Examples of the other component include surfactants, moisturizing agents, polymers, dyes, lower alcohols, polyhydric alcohols, antioxidants, ultraviolet absorbers, cosmetic components, antibacterial agents, preservatives, pH-adjusting agents, fragrance and the like.

The cosmetic of the invention can be used in any of the forms of a powder cosmetic, cream, milky lotion, lotion, an oil-based liquid cosmetic, an oil-based solid cosmetic, a paste cosmetic and the like. Because the feeling upon use is excellent when the cosmetic is applied to the skin, a powder cosmetic is preferable. The powder cosmetic includes a powder solid cosmetic and loose powder and is most preferably loose powder.

Regarding the use of the cosmetic of the invention, for example, the cosmetic can be a makeup cosmetic such as foundation, a concealer, face powder (loose powder or pressed powder), a control color, eye shadow, eye liner, blusher, body powder, perfume powder and baby powder or the like.

EXAMPLES

The invention is explained further specifically below referring to Examples and Comparative Examples. The amounts are described with mass % based on the systems in which the components are blended unless otherwise specified.

[Preparation of Magnesium Myristate 1]

Into a 10-L separable flask, 500 g of myristic acid (NAA-142 manufactured by NOF Corporation) and 5600 g of water were charged, and the temperature was increased to 90° C. Next, 250.0 g of 48 mass % aqueous sodium hydroxide solution was added and stirred at the same temperature (90° C.) for an hour, and thus an aqueous fatty acid-alkaline compound salt solution was obtained. Then, while maintaining at 90° C., 750.0 g of 22 mass % aqueous magnesium sulfate solution was dropped to the aqueous sodium myristate solution over 40 minutes [dropping speed: 0.016 (mol/minute)]. After the completion of dropping, the mixture was maintained at 90° C. and stirred for 30 minutes for aging. The obtained aqueous fatty acid magnesium salt solution slurry was cooled to 65° C. or lower. Then, the mixture was filtered with a suction filter, followed by washing eight times with 1000 g of water, and the obtained cake was dried at 60° C. using a ventilated tray dryer and crushed in a mill. Thus, magnesium myristate particles were obtained.

[Assessment of Magnesium Myristate Particles]

The median size, the particle size digest A [the value calculated from the 10% cumulative size D10 (μm) on a volumetric basis, the median size D50 (μm) on a volumetric basis and the 90% cumulative size D90 (μm) on a volumetric basis], the average thickness of the particles, the major axis diameter, the minor axis diameter and the aspect ratio of the magnesium myristate particles 1 were measured using the following devices by the methods described above.

(1) Particle Size Digest A and Median Size

A sample in an amount of 2.0 g was taken in a 100-ml glass beaker, and 3 to 5 ml of a nonionic surfactant (example; Nonion NS-210 manufactured by NOF Corporation) was dropped and blended with a spatula. Next, 20 ml of purified water was added, and the sample was dispersed by ultrasonic wave. The volume was adjusted to 100 ml, and thus a measurement sample was obtained. The sample was fed to and measured with a particle size distribution analyzer (machine name "Microtrac MT-3000" manufactured by Nikkiso Co., Ltd.) (principle: laser diffraction/scattering method).

A cumulative curve was drawn in which the total volume of the powder population measured was regarded as 100%, and the particle sizes at 10%, 50% and 90% of the cumulative curve were determined as the 10% size (D10), the 50% size (D50; median size) and the 90% size (D90) (μm), respectively. The particle size digest A was determined from the obtained D10, D50 and D90.

(2) Average Thickness of Particles, Major Axis Diameter, Minor Axis Diameter, Aspect Ratio and Particle Index The thickness of the particles was measured by the following method using a scanning electron microscope. A sample obtained by adhering fatty acid magnesium salt particles on a double-sided carbon tape and then coating the particle surfaces with platinum particles by vapor deposition was observed at an acceleration voltage of 1.0 kV and at 2000× magnification, and the thicknesses of particles were measured at random. The thicknesses, the major axis diameters and the minor axis diameters of 10 particles at random were determined. Moreover, the aspect ratio and the particle index were determined by the following formulas.

$$\text{Particle Index}=[(\text{Major axis diameter } (\mu m)/\text{Minor axis diameter } (\mu m))/\text{Average Thickness of Particles } (nm)]\times 1000$$

$$\text{Aspect Ratio}=\text{Major axis diameter } (\mu m)/\text{Minor axis diameter } (\mu m)$$

The measurement results are shown below.

<Properties of Magnesium Myristate Particles 1>

Aspect ratio: 1.4
Particle index: 4.7
D10: 11.4 μm
D50: 25.3 μm
D90: 54.9 μm
Average thickness of particles: 309 nm
Particle size digest A: 1.7

[Magnesium Myristate 2]

For comparison, magnesium myristate having an aspect ratio of 2.52 and a median size (D50) of 17 μm (manufactured by Taihei Chemical Industrial Co., Ltd.) was prepared.

[Zinc Myristate]

For comparison, zinc myristate having an aspect ratio of 2.38, a median size of 10 μm and an average thickness of 304 nm (manufactured by Nippon Oil & Fats Co., Ltd., zinc myristate) was prepared.

Example 1 and Comparative Examples 1 to 4: Loose Powders

Loose powders having the compositions shown in Table 1 were prepared according to the following production method.

Production method: Powder excluding the oil component (liquid oil component: silicone oil) was mixed using a Henschel mixer and mixed again with the Henschel mixer after the addition of the oil component. The obtained mixture was packed in a container with a mesh.

[Assessment of Use Feeling]

The feeling upon use and the like of the cosmetic (loose powder) obtained by the invention were assessed based on the following criteria. The results are shown in Table 1.

(1) Moistness

Ten expert analysts determined the moistness when the cosmetic was applied to the skin as follows, and the moistness was determined to be excellent in the case of A or B.

A: Moistness is felt extremely.
B: Moistness is felt.
C: Moistness is not felt so much.
D: Moistness is not felt. Squeakiness is felt.

(2) Transparency

Ten expert analysts determined the transparency when the cosmetic was applied to the skin as follows, and the transparency was determined to be excellent in the case of A or B.

A: natural finishing with little whiteness
B: natural finishing despite slight whiteness
C: slightly unnatural finishing with whiteness
D: unnatural finishing with considerable whiteness (3) Gloss Ten expert analysts determined the gloss when the cosmetic was applied to the skin as follows, and the gloss was determined to be excellent in the case of A or B.

A: very glossy
B: glossy
C: slightly glossy
D: not glossy

TABLE 1

| | Example 1 | Comparative Example 1 | Comparative Example 2 | Comparative Example 3 | Comparative Example 4 |
|---|---|---|---|---|---|
| Mica | 16 | 16 | 16 | 16 | 16 |
| Synthetic Mica | 38.5 | 38.5 | 38.5 | 38.5 | 38.5 |
| Synthetic fluorphlogopite iron | 4.5 | 4.5 | 4.5 | 4.5 | 4.5 |
| Metallic Soap-Treated Synthetic Mica | 10 | 10 | 10 | 10 | 10 |
| Magnesium Myristate 1 | 19 | 19 | 19 | — | — |
| Magnesium Myristate 2 | — | — | — | 19 | — |
| Zinc Myristate | — | — | — | — | 19 |
| Lauroyl Lysine | 2 | 2 | 2 | 2 | 2 |
| Titanium Oxide 1 | 1 | — | — | 1 | 1 |
| Titanium Oxide 2 | — | 1 | — | — | — |
| Talc | 7.1 | 7.1 | 7.1 | 7.1 | 7.1 |
| Preservative | 0.2 | 0.2 | 0.2 | 0.2 | 0.2 |
| Silicone Oil | 1 | 1 | 1 | 1 | 1 |
| Color Material 1 | 0.15 | 0.15 | 0.15 | 0.15 | 0.15 |
| Color Material 2 | 0.55 | 0.55 | 0.55 | 0.55 | 0.55 |
| Moistness | A | A | C | B | C |
| Transparency | A | C | B | D | C |
| Gloss | A | A | A | C | D |

Metallic soap-treated synthetic mica: Mg stearate-treated synthetic fluorphlogopite Lauroyl lysine: Amihope LL (registered trademark) manufactured by Ajinomoto Co., Inc.

Titanium oxide 1: MT-100TV manufactured by Tayca Corporation (fine particle titanium oxide having an average particle size of 0.015 μm)

Titanium oxide 2: triethoxycaprylylsilane-treated titanium oxide (OTS-treated CR-50 manufactured by Daito Kasei Kogyo Co., Ltd., titanium oxide having an average particle size of 0.25 μm)

Color material 1: yellow iron oxide

Color material 2: red iron oxide

From the above results, it is seen that the cosmetic of the Example, which contains magnesium myristate particles having specific properties and fine particle titanium oxide, has excellent feeling upon use.

Example 2 and Comparative Examples 5 to 8

Pressed powders having the compositions shown in Table 2 were prepared according to the following production method.

Production method: Powder excluding the oil components (semi-solid oil component: Vaseline and liquid oil components: triisostearin, triethylhexanoin and ethylhexyl methoxycinnamate) and the active agent (sorbitan sesquiisostearate) was mixed using a Henschel mixer and mixed again with the Henschel mixer after the addition of the oil components and the active agent. The obtained mixture was pulverized using an atomizer and pressed with a forming machine.

[Assessment of Use Feeling]

The feeling upon use and the like of the cosmetic (pressed powder) obtained by the invention were assessed based on the same criteria as those of Example 1. The results are shown in Table 2.

TABLE 2

| Component Name | Example 2 | Comparative Example 5 | Comparative Example 6 | Comparative Example 7 | Comparative Example 8 |
|---|---|---|---|---|---|
| Mica | 10 | 10 | 10 | 10 | 10 |
| Synthetic fluorphlogopite | 15 | 15 | 15 | 15 | 15 |
| Magnesium Myristate 1 | 6 | 6 | 6 | — | — |
| Magnesium Myristate 2 | — | — | — | 6 | — |
| Zinc Myristate | — | — | — | — | 6 |
| Titanium Oxide 1 | 7.5 | — | — | 7.5 | 7.5 |
| Titanium Oxide 2 | 4 | 11.5 | — | 4 | 4 |
| Talc | 4.1 | 4.1 | 15.6 | 4.1 | 4.1 |
| Metallic Soap-Treated Talc | 7 | 7 | 7 | 7 | 7 |
| Silicone-Treated Talc | 24.5 | 24.5 | 24.5 | 24.5 | 24.5 |
| Hydrophobized Silica | 2 | 2 | 2 | 2 | 2 |
| Nylon-12 | 3 | 3 | 3 | 3 | 3 |
| PMMA (polymethyl methacrylate) | 4 | 4 | 4 | 4 | 4 |
| Calcium Carbonate | 2 | 2 | 2 | 2 | 2 |
| Color Material 1 | 1.18 | 1.18 | 1.18 | 1.18 | 1.18 |
| Color Material 2 | 0.32 | 0.32 | 0.32 | 0.32 | 0.32 |
| Preservative | 0.2 | 0.2 | 0.2 | 0.2 | 0.2 |
| Vaseline | 1 | 1 | 1 | 1 | 1 |
| Sorbitan Sesquiisostearate | 0.8 | 0.8 | 0.8 | 0.8 | 0.8 |
| Triisostearin | 1 | 1 | 1 | 1 | 1 |
| Triethylhexanoin | 1.4 | 1.4 | 1.4 | 1.4 | 1.4 |

TABLE 2-continued

| Component Name | Example 2 | Comparative Example 5 | Comparative Example 6 | Comparative Example 7 | Comparative Example 8 |
|---|---|---|---|---|---|
| Ethylhexyl Methoxycinnamate | 5 | 5 | 5 | 5 | 5 |
| Moistness | A | A (squeakiness) | C | B | C |
| Transparency | A | D | B | C | D |
| Gloss | B | C | B | C | C |

Titanium oxide 1: MT-100TV manufactured by Tayca Corporation (fine particle titanium oxide having an average particle size of 0.015 μm)

Titanium oxide 2: triethoxycaprylylsilane-treated titanium oxide (OTS-treated CR-50 manufactured by Daito Kasei Kogyo Co., Ltd., titanium oxide having an average particle size of 0.25 μm)

Color material 1: yellow iron oxide

Color material 2: red iron oxide

From the above results, it is seen that the cosmetic of the Example, which contains magnesium myristate particles having specific properties and fine particle titanium oxide, has excellent feeling upon use.

Although the invention has been explained in detail referring to specific embodiments, it is obvious to one skilled in the art that various changes and modifications can be made without departing from the spirit and the scope of the invention.

The invention claimed is:

1. A cosmetic containing fatty acid magnesium salt particles and fine particle titanium oxide, wherein the fatty acid of the fatty acid magnesium salt particles has 12 to 22 carbon atoms, an aspect ratio of the fatty acid magnesium salt particles defined for an individual particle as a ratio between a major axis diameter of the particle and a minor axis diameter of the particle is 1.0 or more and 2.0 or less, and the average thickness of the fatty acid magnesium salt particles is 250 to 600 nm.

2. The cosmetic according to claim 1 which further contains an oil-based component.

3. The cosmetic according to claim 1, wherein the fine particle titanium oxide content is 10 mass % or less.

4. The cosmetic according to claim 2 which contains a liquid oil-based component as the oil-based component.

5. The cosmetic according to claim 2, wherein the oil-based component content is 10 mass % or less.

6. The cosmetic according to claim 1, wherein the cosmetic is a powder cosmetic.

* * * * *